(12) United States Patent
Flores et al.

(10) Patent No.: US 7,632,295 B2
(45) Date of Patent: Dec. 15, 2009

(54) FERROELECTRIC HYPERTHERMIA METHOD FOR CANCER TREATMENT

(75) Inventors: Glen Patrick Flores, Gainesville, FL (US); Christopher D. Batich, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 675 days.

(21) Appl. No.: 11/512,528

(22) Filed: Aug. 29, 2006

(65) Prior Publication Data

US 2006/0293729 A1    Dec. 28, 2006

Related U.S. Application Data

(62) Division of application No. 10/889,871, filed on Jul. 13, 2004, now Pat. No. 7,122,030.

(51) Int. Cl.
*A61F 7/00* (2006.01)
*A61F 7/12* (2006.01)
*A61B 18/04* (2006.01)

(52) U.S. Cl. .............................. 607/96; 607/113; 606/27

(58) Field of Classification Search .................. 607/96, 607/101, 113; 606/27
See application file for complete search history.

(56) References Cited

U.S. PATENT DOCUMENTS

| | | | |
|---|---|---|---|
| 5,067,952 A | 11/1991 | Gudov et al. | |
| 5,928,224 A | 7/1999 | Laufer | |
| 6,099,457 A | 8/2000 | Good | |
| 6,258,249 B1 | 7/2001 | Simpson | |
| 6,611,719 B2 | 8/2003 | Saito | |
| 2003/0028071 A1 | 2/2003 | Handy et al. | |
| 2003/0088145 A1 | 5/2003 | Scott | |
| 2003/0219384 A1 | 11/2003 | Donath et al. | |

OTHER PUBLICATIONS

Lee et al. "Clinical experience using 8 MHZ radiofrequency capacitive hyperthermia in combination with radiotherapy: results of phase I/II study", Int. J. Radiation Oncology Biol. Phys., vol. 32, No. 3, 1995, pp. 773-745.
Kotsuka et al. "Development of double-electrode applicator for localized thermal therapy", IEEE Transactions on Microwave Theory and Techniques, vol. 48, No. 11, 2000, pp. 1906-1908.

*Primary Examiner*—Roy D Gibson
*Assistant Examiner*—Kaitlyn E Helling
(74) *Attorney, Agent, or Firm*—Saliwanchik, Lloyd & Saliwanchik

(57) ABSTRACT

A method of localized cell heating introduces a plurality of ferroelectric comprising particles into a target region of a patient, and applies a time varying electrical field to the target region. The ferroelectric particles absorb energy from the electrical field and heat the target region in response, such as to a temperature sufficient to induce apoptosis of cancer cells in the target region. A ferroelectric hyperthermia-based cancer treatment system includes a time varying electrical field source for applying a time varying electrical field to a plurality of ferroelectric particles disposed in a target cancer containing region of a patient. A composition of matter includes a particle having a ferroelectric portion, the particle being non-toxic, slowly biodegradable in body fluids, and less than 15 µm in its maximum dimension.

10 Claims, 7 Drawing Sheets

FERROELECTRIC HYPERTHERMIA METHOD FOR CANCER TREATMENT

CROSS-REFERENCE TO RELATED APPLICATIONS

This application is a divisional of U.S. patent application Ser. No. 10/889,871 filed Jul. 13, 2004, entitled "FERROELECTRIC HYPERTHERMIA SYSTEM AND METHOD FOR CANCER THERAPY", the entirety of which is incorporated herein by reference.

STATEMENT REGARDING FEDERALLY SPONSORED RESEARCH OR DEVELOPMENT

Not applicable.

FIELD OF THE INVENTION

The invention relates to the treatment of tissue including cancerous tumors, and, more specifically, to systems and methods for implanting ferroelectric particles into tumorous tissue regions and heating such tissue using applied electrical fields.

BACKGROUND

Hyperthermia (HT) is a cancer treatment that utilizes heat to destroy cancerous tumors. The past two decades have offered new advances in HT to varying degrees of success. Although HT is still an experimental treatment in the United States and is usually only applied to late-stage cancer patients, international HT results from various countries give more promise to this treatment. The major arguments for local and regional HT result from patients with locally advanced malignancies, where increased response and survival rates have been shown using HT combined with radiotherapy in phase-III trials as compared to radiation alone.

Technical problems still exist regarding different HT approaches, therapeutic potential, and evidence of effectiveness. The foremost problem is generally related to generating and controlling the temperature applied to the tumors and the surrounding tissue. A sufficiently high temperature is needed for inducing programmed cell death (apoptosis) of the tumor cells, but too high a temperature is known to cause neighboring normal cells to undergo necrosis, or otherwise become damaged. The currently accepted target window of temperatures for HT is between about 42° C. and 45° C., with 43° C. considered to be the ideal temperature for apoptosis of tumor cells without harming neighboring normal cells.

To address HT control problems, various methods have been utilized to localize HT heating and limit its temperatures through various applicators, materials, and procedures. One method has been to implant ferromagnetic materials into the human body proximate to tumor sites to cause the ferromagnetic particles to heat up responsive to an externally applied magnetic field. This process is known as interstitial HT (IHT) as it uses interstitial particles or related ferromagnetic thermoseeds. The ferromagnetic material generally comprises particles such as iron oxide or various nickel compounds.

The use of interstitial particles has been extensively researched, with results as early as 1971 using thermally self-regulating implants to produce brain lesions. This method is particularly useful for delivering thermal energy to deep seated tumors. These implants have been shown to heat surrounding tissue until they reach a Curie temperature at which heating is no longer produced. However, most ferromagnetic (FM) materials are toxic even in low concentrations and quite soft and thus require a biocompatible encapsulating coating layer. Unfortunately, the coating layer can adversely effect efficacy of procedure. Moreover, FM particles are generally non-biodegradable and thus either remain in the treatment location or require a difficult removal process.

SUMMARY

The invention uses ferroelectric (FE) comprising particles for non-toxic interstitial HT treatment. The class of materials known as ferroelectrics provides improved biocompatibility as compared to ferromagnetic compositions, thus leading to better heat administration at tumor sites. As a result of the procedure, a sufficiently high temperature is produced around the tumor cite for inducing programmed cell death (apoptosis) of the tumor cells without harming neighboring normal cells.

A method of localized cell heating includes the steps of introducing a plurality of ferroelectric comprising particles into a target region of a patient, and applying a time varying electrical field to the target region. The ferroelectric particles absorb energy from the electrical field and heat the target region in response. The electrical field can be a pulsed electrical field.

In a preferred embodiment, the ferroelectric exhibits a Curie Temperature (Tc) in a therapeutic range between 41.5° C. and 50° C. The ferroelectric particles can comprise TGS. In an alternate embodiment, the ferroelectric particles can comprise at least two different ferroelectric materials, such as doped TGS.

The particles can comprise a non-ferroelectric coating layer on ferroelectric cores. The coating layer can comprise a bio-compatible and biodegradable polymer, such as PLGA, PLA or PGA. At least one drug can be included beneath the coating layer. In a preferred readily injectable embodiment, the plurality of particles have an average largest dimension of less than 15 μm and are disposed in a pharmaceutically suitable solution. The introducing step can comprises injection of the solution into the target region of the patient, such as injection into a blood vessel which feeds a tumor, such as the hepatic artery. Alternatively, direct injection can be used, analogous to conventional application of cytotoxic agents.

A ferroelectric hyperthermia-based cancer treatment system includes a time varying electrical field source for applying a time varying electrical field to a plurality of ferroelectric particles disposed in a target region of a patient. The target region includes or is believed to include cancer cells. A guidance tool directs the electric field to the target region. The ferroelectric particles absorbs energy from the electrical field and heat the cancer cells to a temperature sufficient to induce apoptosis or necrosis of the cancer cells.

The system can include a temperature detector for measuring the temperature in the target region. The system can include a feedback and control system communicably connected to the temperature detector. The feedback and control system holds the temperature within a predefined range of temperatures and automatically controls at least one parameter of the time varying electrical field source to maintain a desired temperature range. The time varying electrical field source can comprise a power supply coupled to a pair of electrically conductive plates, wherein the target region is disposed between the plates.

In one embodiment, the time varying electrical field source can comprise an RF generator coupled to an antenna. The electrical field source can be a pulsed electrical field source.

A composition of matter comprises a particle including at least a ferroelectric portion. The particle is non-toxic, and slowly degradable in body fluids. In one embodiment, the particle is between 1 and 100 μm in its maximum dimension, such as diameter in the case of a spherical particle. The maximum dimension is preferably generally between 5 and 10 μm. The plurality of particles can be suspended in a pharmaceutically suitable solution well adapted for injection. As used herein, the phrase "slowly degradable" refers to a residence time within the body prior to complete dissolution of at least 30 minutes, but less than 14 days.

The ferroelectric can provide a Tc of between 41.5° C. and 50° C. In one embodiment, the ferroelectric comprising particle comprises a ferroelectric core and a non-ferroelectric coating layer disposed on the core. A drug can be disposed beneath the coating layer. The ferroelectric core can comprises TGS. In an alternate embodiment, the ferroelectric core can comprises at least two different ferroelectric materials.

BRIEF DESCRIPTION OF THE DRAWINGS

A better understanding of the present invention can be obtained when the following detailed description is considered in conjunction with the following drawings in which.

DETAILED DESCRIPTION

A method of localized cell heating includes the steps of introducing a plurality of ferroelectric comprising particles into a target location within a patient and applying an electrical field. The electrical field is preferably a time varying electrical field, such as the electrical field produced by application of a time varying potential across the electrically conductive plates of a capacitor. The applied electrical field strength should at least the coercive field strength of the specific FE material used to cause the desired polarization switching.

The capacitor can be disposed external to the body of the patient, or be disposed internal to the body, such as using implanted electrodes, analogous to the TENS device. Alternatively, a time varying electrical field can be provided by a radiation generator along with an associated oscillator coupled to a suitable antenna which emits electromagnetic waves. Electromagnetic waves consist of oscillating electric and magnetic fields and should be selected in a frequency range which permits sufficient transmission though the body of the patient to the tumor cite. The ferroelectric particles absorb energy from the applied electrical field and heat up in response. The resulting ferroelectric induced heating produces temperatures sufficient to induce apoptosis or necrosis of target cells, such as tumor cells, but low enough to prevent normal cells from being damaged.

Ferroelectrics are a class of materials that relate to crystalline dielectrics that can be given a permanent electric polarization by application of an electric field. Such materials exhibit spontaneous polarization and show temperature-limiting behavior. The Curie temperature ($T_C$) of a ferroelectric is a temperature at which received electromagnetic radiation will no longer measurably heat the ferroelectric material. These materials heat via hysteresis losses under applied electric fields (E-field), making it possible to heat the ferroelectric particles using radiation received from time-varying electrical fields, such as the field radiated from a suitably driven radiofrequency (RF) antenna or generated between the plates of a capacitor driven by a time-varying wave form.

Figure 1:
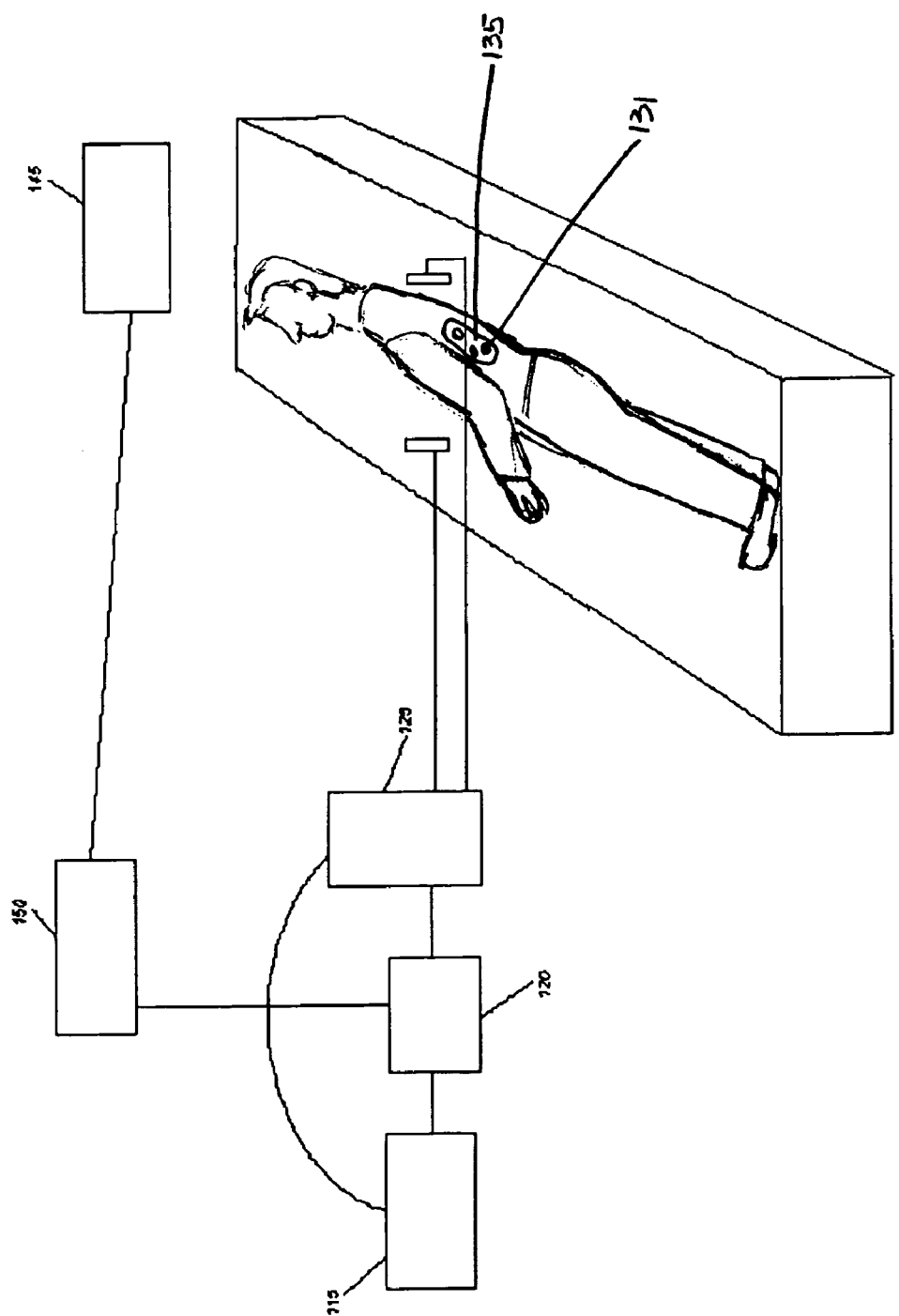
FIG. 1 is a diagram of a FE-based hyperthermia treatment system including a pair of external electrodes, according an embodiment of the invention.

FIG. 1 is a block diagram of a FE-based hyperthermia treatment system 100 according to an embodiment of the invention is shown. Patient 130 has a malignant tumor 135. In a process step performed prior earlier, the location of tumor 135 was identified and ferroelectric particles 131 according to the invention were introduced proximate to tumor 135, such as via a syringe with 5 to 30 μm FE particles in a suitable suspension guided by a conventional optical guidance system. Ferroelectric particles 131 heat up responsive to exposure to the applied time varying electrical field. In some cases, it may be desirable to activated the FE material to maximize spontaneous polarization using a time-varying electrical field after synthesis, but before injection or other introduction method.

System 100 includes a pair of electrically conductive plates 105 and 110 which together form a capacitor. Capacitor plates 105 and 110 preferably include a circulating water pad or other cooling arrangement to prevent burning of the skin of the patient (not shown). Power supply 115 together with function generator/oscillator 120 and power amplifier 125 provide a time varying voltage signal across the plates 105 and 110. The voltage signal generates a time varying electrical field which reaches target region 135 of patient 130.

The parameters of the voltage signal applied, such as frequency, duty cycle and power, will be generally based on the electrical field required to attain a desired tumor temperature. As the separation distance between the plates 105 and 110 is increased, the required voltage will correspondingly increase. The desired temperature is generally about 43 C, which is generally sufficient to induce apoptosis of target cells, such as tumor cells, but low enough to prevent normal cells from being damaged.

System 100 shown in FIG. 1 includes structure for measuring the temperature 145 proximate to tumor 135, and a feedback and control system 150 which automatically controls power supply 115 or function generator/oscillator 120 and power amplifier 125 to maintain the desired tumor temperature. For example, the structure for measuring temperature 145 can be an infrared thermometer for measuring the tumor temperature. Nuclear magnetic resonance (NMR) may also be used. In one embodiment, a fiber optic light pipe having a temperature sensor on its distal end may be inserted into the tumor region of the patient.

Figure 2:
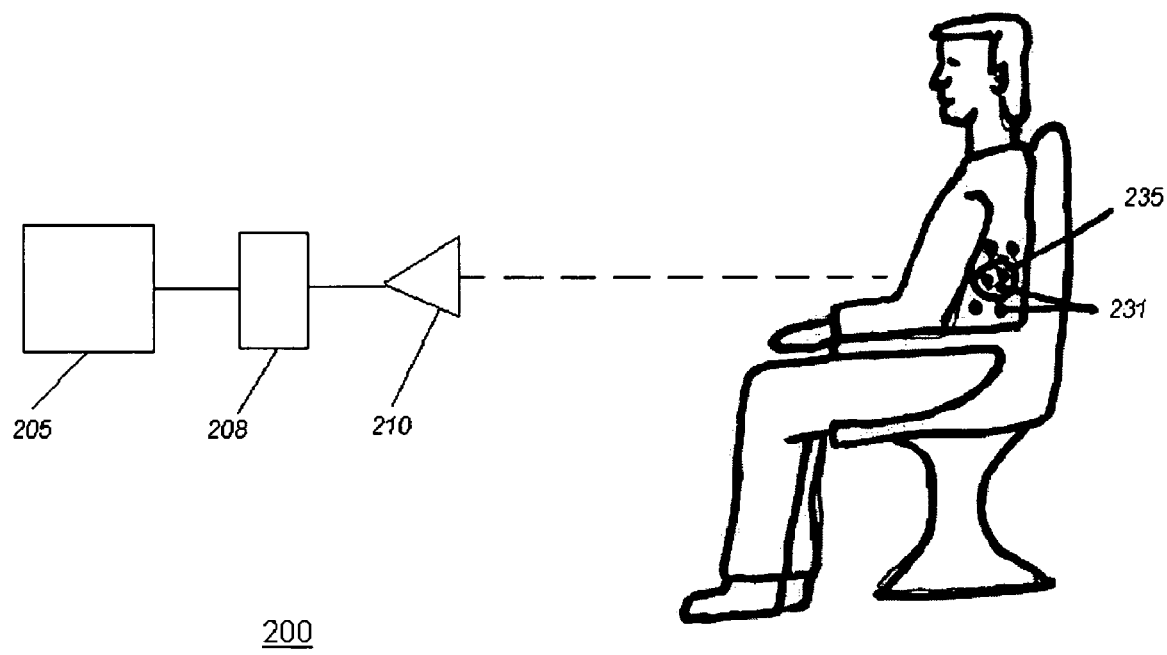
FIG. 2 is a diagram of a FE-based hyperthermia treatment system including a radiation generator and radio frequency antenna, according an another embodiment of the invention.

Now turning now to FIG. 2, a block diagram of a FE-based hyperthermia treatment system 200 according to another embodiment of the invention is shown. System includes a power supply/radiation generator 205 which is generally a non-ionizing radiation generator, such as an RF generator.

Figure 3:
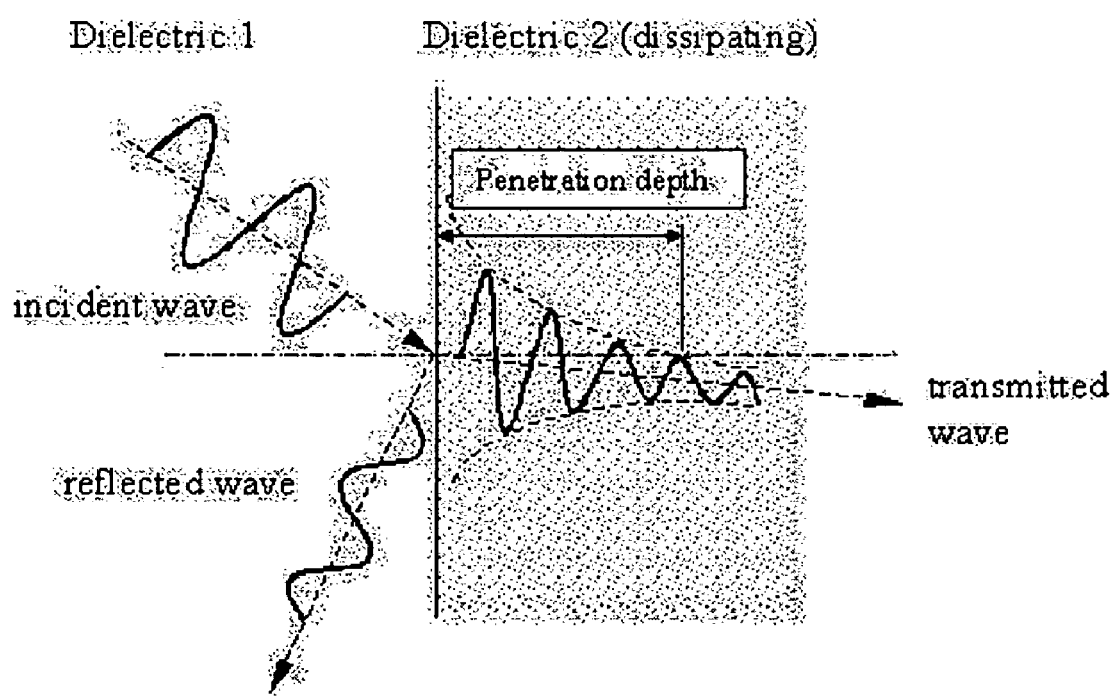
FIG. 3 shows the wave dynamics occurring on the surface (interface between dielectric 1 and 2) and inside the lossy tissue (dielectric 2) comprising media resulting from irradiation of the interface.

The frequency provided by generator 205 is selected to provide a sufficient penetration depth to reach tumor 135. The penetration depth is defined as the distance measured from the skin being surface of the medium, where the amplitude of the electrical field decreases to 1/e of the value on the surface. This is approximately 0.37 of the original magnitude. FIG. 3 shows the wave dynamics occurring on the surface (interface between dielectric 1 and 2) and inside the lossy tissue (dielectric 2) comprising media resulting from irradiation of the interface.

Since the penetration depth of radiation into human tissue is known to decrease quickly at frequencies above 100 MHz, the frequency used will generally be at least 100 kHz to about 100 MHz. In one embodiment, the frequency used is around 1 MHz.

Generator 205 is coupled to transmitter 208 which drives antenna 210. Antenna emits electromagnetic waves in the direction of a target region within a patient 230. Antenna 210 can be an antenna array. Ferroelectric particles 231 are disposed within and adjacent to a tumor 235 within patient and heat responsive to exposure to the incident electrical field. As noted relative to system 100, system 200 can include structure for measuring the temperature proximate to tumor 235 (not shown), and a feedback and control system (not shown) which automatically controls power supply 205 to maintain the desired tumor temperature, such as within the therapeutic range between 41.5° C. and 50° C.

Preferred ferroelectrics for use with the invention for apoptosis of target cells provide a Curie temperature in the range from about 42 to 46° C. However, through the use of pulsed electrical fields, ferroelectrics having higher Curie temperatures can be used together when suitable control is provided which turns off the applied electrical field when the desired tumor temperature is reached and turns the electrical field back on upon reaching some lower temperature set point. More generally, by selecting a pulse duration and a spacing between pulses, and taking into account the thermal relaxation or thermal dissipation rates of the surrounding tissue, the pulse width and pulse spacing can be optimized to maintain a predetermined temperature.

For ablation applications of the invention, higher temperatures are generally required. The range from 46° C. to 100° C. is the ablation range wherein tissue is damaged or destroyed from the heat itself.

Ferroelectric triglycine sulfate $(NH_2CH_2OOH)_3H_2SO_4$ (hereafter TGS) has a $T_C$ of about 49° C. TGS may be doped with a suitable amount of Se to provide a Curie temperature in the desired temperature range. TGS is a highly water soluble crystal that is known to be biodegradable and biocompatible in the human body.

TGS shows an increasing dielectric-constant with temperature and strong dielectric loss peaks that rise with temperature. Since the $T_C$ for TGS occurs at 49° C., the maximum for the dielectric constant coincides with $T_C$. Along the polar axis, TGS shows a rather large peak dielectric constant of $1 \times 10^5$ at 500 kHz and 1 V/cm, which is much larger than its room temperature value of 43. As the dielectric constant increases, spontaneous polarization, the target source of heating for HT through hysteresis losses, decreases to zero at $T_C$.

The heat capacity, $C_p$, for TGS shows a Curie point type of behavior. $C_p$ increases as the temperature is raised, which may be beneficial for TGS to maintain its heat at higher temperatures and losing the ability to maintain heat at temperatures higher than $T_C$ so as not to overheat the tissue.

Barium titanate (BT) is another FE material that can also be used with the invention. BT can be doped with strontium titanate or other dopants to reduce the $T_C$ of the resulting composite material. Barium titanate (hereafter BT) shares the perovskite crystal structure with many other well known FEs, including lead titanate, lead zirconium titanate, and potassium niobate. Significantly, BT can be used as a contrast agent which can assist in aligning the radiation filed to the tumor after the BT comprising particles are introduced into the tumor.

The BT paraelectric phase has cubic symmetry at temperature above its Curie point (about 120° C.). Between the temperatures of 0° C. and 120° C., BT has a tetragonal FE phase with c/a of about 1.01 being stable and spontaneous polarization along the c-axis of the tetragonal unit cell. Below 0° C., an orthorhombic crystal phase becomes stable. Finally, at 90° C., the phase transition of BT changes once more as the orthorhombic phase cools to the rhombohedral phase.

The coating of water soluble FEs is generally required for clinical use of FE interstitials since the human body is about 70% water. For water soluble ferroelectrics such as TGS, the ferroelectric composition can be coated with non-water soluble coatings to provide protection against aqueous environments with bio-compatible and biodegradable polymeric materials, such as Polylactic acid (PLA), polyglycolic acid PGA, poly-(lactide co-glycolide) acid (PLGA), as well as various cellulose comprising compounds. Other possible coatings include polycaprolactone, polyurethanes, and or other polyesters.

The coatings can be either continuous and non-porous coatings, or discontinuous and porous coatings. Some degree of porosity may be desirable since porosity allows implanted particles to dissolve and be excreted following treatment. Although biodegradable shells can be used to protect soluble ferroelectric particles from dissolution, certain ferroelectric particles that may be suitable for hyperthermia are not soluble and therefore need no such shell.

In the case of particles comprising coated toxic FE materials, such materials are generally preferably coated with non-biodegradable shells. Such particles are then generally removed following therapy.

Different coated particle arrangements are possible. In one embodiment, generally single FE particles are each coated by a coating layer. In another embodiment, a plurality of FE particles are held together with a coating material analogous to a plumb pudding arrangement.

FE materials can be coated using a variety of methods. For example, TGS can be coated with a surfactant and then an oil-in-oil process (e.g. with chloroform) can be used to coat FE powders with coatings such as PLGA or PLA. Other coating methods including spray methods may be used.

The particle size, including the optional coating, is generally selected to be small enough to permit the particles to maneuver through capillaries. In a preferred embodiment, particles generally have maximum dimensions (diameter in the case of spherical particles) of generally <15 μm, such as <10 μm, to ensure that the particles become embedded in capillary beds surrounding the tumors. A preferred particle size for this purpose is generally between 3 and 10 μm. Such particles, when in a pharmaceutically acceptable carrier are readily injectable. However, in some non-injectable applications, use of larger particles may be necessary.

Preferred ferroelectric comprising particles are non-toxic. Such particles also slowly degradable in body fluids, such as blood and water.

Coated FE particles can also optionally include one or more drugs disposed under the coating. The drug may comprise an anti inflammatory agent, an anti proliferative agent, or an antibiotic. For example, lipiodol can be incorporated for the targeted treatment of hepatocellular carcinoma.

Hyperthermia according to the invention can be used alone or in combination with other treatment modalities. For example, the invention can be used in conjunction with radiotherapy or chemotherapy. The synergy of hyperthermia and ionizing radiation has been reported in the treatment of several types of tumors.

Treatment planning for interstitial HT according to the invention generally involves three different aspects. First, the target volume is determined in a process referred to as target definition. Second, the location and distribution of the implanted particles are determined with respect to the anatomy in the target volume vicinity. This process is referred to as implant configuration. Third, the temperature distribution in tissue during treatment is calculated from the power deposition distribution in a process referred to as thermal dosimetry.

A treatment planning system for interstitial HT may be used. The planning system preferably uses individual patient data, which can be obtained from imaging, such as available from 3-D MR acquisitions or tomography. In an alternate imaging method, a digestible contrast agent is used. For example, ethiodol is known to be digested by healthy liver portions but is poorly digested by a damaged cancerous liver. Accordingly, imaging performed a suitable period after application of ethiodol to allow digestion by normal liver cells can allow tumor ridden liver areas to be readily identified.

In another embodiment, some particles may be capable of preferentially adhering to cancer cells. For example, certain cancer cells are known to adhere to certain amino acids. For example, folic acid (pteroylglutamic acid), which is a B vitamin needed for cell replication and growth, is known to adhere to cancer cells. Cancer cells can also be bound by suitable antibodies. Once bound, the locations of cancerous tumors can be identified by known methods.

The planning system generally consists of a number of tools for tasks such as delineating the target volume, defining the implant configuration, and calculating the power deposition and temperature distribution. An important characteristic of the planning system is that it is fully anatomy based. Individual patient data, such as the dielectric and thermal anatomy and the arterial and venous vessel networks, are preferably used as input for the calculation models.

The FE particles are then generally applied using a guidance tool, such as optical markers known in the art. For example, a syringe including a suspension of FE particles according to the invention can be computer guided to the tumor cite using the image guidance tool and then used to dispense the suspension. It may also be possible to inject the FE particles directly in a target location without a guidance tool, or even be breathe in as an aerosol for lung cancer treatment. The FE hyperthermia process can then be begun using a suitable system, such as system 100.

Although described for the treatment of cancer, the invention is not limited to cancer treatment. For example, the invention can be used to treat varicose veins. In this embodiment FE particles can be placed in the area(s) to be treated, such as using a syringe. FE induced heating can treat this condition through localized heating, analogous to conventional laser treatments.

EXAMPLES

The present invention is further illustrated by the following specific examples, which should not be construed as limiting the scope or content of the invention in any way.

In the examples presented, an inductor was used to create E-fields therein via induction from the induced H-fields which resulted in heating of the FE material. Although this arrangement is generally not practical in a FE hyperthermia therapy system, the data obtained demonstrates that FE particles according to the invention can produce the heating required for effective cancer treatment.

The FE heating system used in the experiments performed included an HP 3312A Function Generator 205 capable of 1 MHz in frequency oscillation, and an AP 400B Controllable Power Amplifier capable of supplying a maximum of 500 W to the load. A Tektronix TDS 3012 & P3010 Oscilloscope and Probe was used to monitor the signal. Two copper constantan thermocouples were used to measure the temperature of the FE sample which was disposed within coil. The coil was wrapped around a ¼" Plexiglas tube and ¼" foam insulation to prevent sample heating by IR radiation and conduction.

The coil size was L=100 mm, d=53 mm, 55 turns. The system provided a narrow bandpass of resonance, with a distinct peak near 955 kHz. A capacitor in parallel with the inductor coil was used to provide a resonant frequency. Another capacitor was used (in series) to allow for different values of resonant frequency.

Four (4) different materials were tested against each other for heating in the same environment. Two were dielectric crystal control samples (non-FE) and other two were BT and TGS. The control samples were NaCl (Fisher Scientific, granular) and $CaCO_3$ (Aldrich Chemical Company) which were both taken directly from pre-made solid powders.

In contrast to control samples, FE samples were prepared to specifications for heating within an inductor. BT was prepared from <10 μm BT powder (Aldrich Chemical Company) into larger particles to better match the size of other particles tested. To accomplish this, the original powder was heated in a furnace up to 1300° C. for 4 hrs within a box furnace. A heating rate of 4° C./min was used to achieve maximum temperature and 4° C./min to cool to room temperature.

TGS samples were prepared following Meera et al. ("Growth and characterization of L-cystine doped TGS crystals," *J Crystal Growth*, 226:303-312, 2001). The Molar ratio of glycine to $H_2SO_4$ was 3:1. Both samples were dissolved into 50 mL $H_2O$ and dried at 45° C. overnight.

Coated TGS particles produced to show that TGS could be, at least in part, be defended against dissolution in aqueous environments such as the human body. 10 (ten) mL of chloroform was mixed with the TGS, and then sonicated to break up larger agglomerations, and finally the PLGA was dissolved into the mixture. The samples were allowed to air dry in small aluminum pans.

Figure 4:
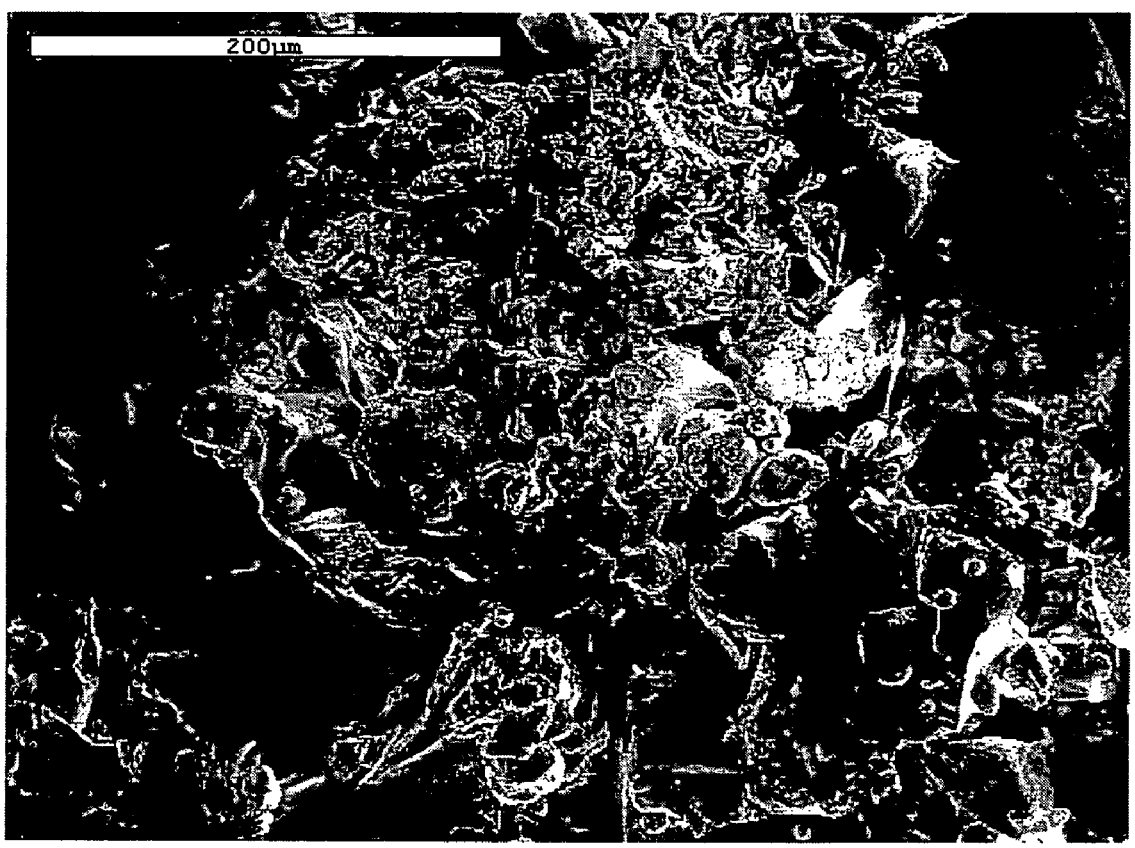
FIG. 4 is a scanned SEM of the ferroelectric TGS within a PLGA coating layer, according to an embodiment of the invention.

FIG. 4 shows a SEM of TGS within a PLGA matrix. The smooth features indicate a polymeric substance (PLGA) that has covered a more rigid one (TGS). This evidences that TGS was indeed covered with PLGA. To check for dissolution TGS dissolution into aqueous environments, samples of TGS/PLGA were submerged in water. PLGA coated samples were found to not dissolve as quickly as uncoated TGS.

The results of various heating tests are given below for TGS, BT, and the dielectric controls comprising $CaCO_3$ and NaCl. The results show the temperature rise effect of FE and non-FE samples using a variety of testing methods.

The results obtained indicate a constant source of temperature rise in TGS over the control ($CaCO_3$). One experiment was designed to show heating in TGS over $CaCO_3$ near room temperature. Thus, random starting temperatures were chosen and the temperature rise was found for each sample, as well as for the insulation temperature. In addition, the thermocouples were tested to see the effects of the RF signal that may cause interference and, therefore, inaccurate readings.

Figure 5:
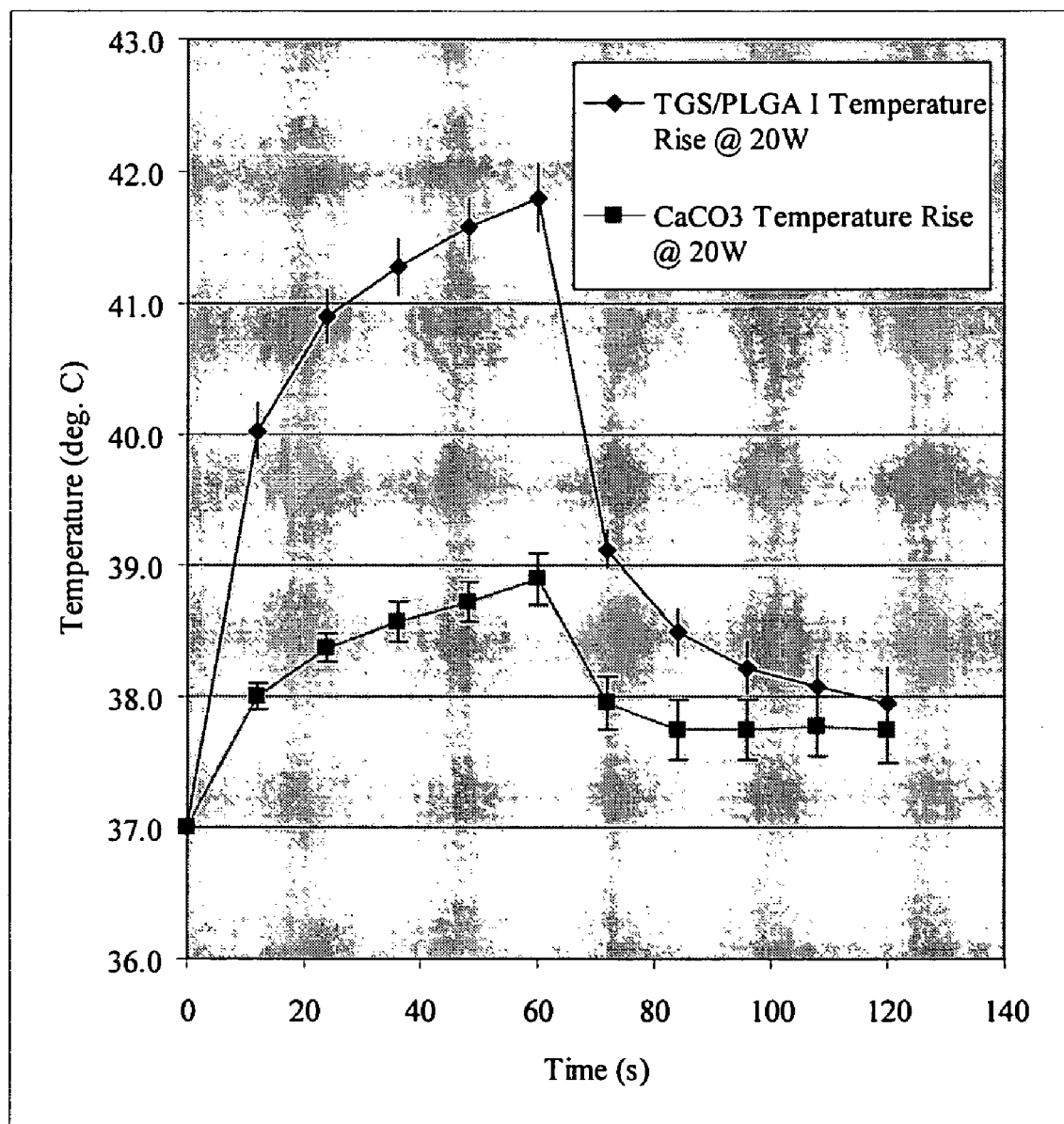
FIG. 5 shows temperature response results obtained from TGS and the $CaCO_3$ control using 20 W and 30 W of applied power.

FIG. 5 shows temperature response results obtained from TGS and the $CaCO_3$ control using 20 W and 30 W of applied power. TGS not only shows a much greater temperature rise, but also a higher temperature soon after the power is shut off from the coil. The larger decrease in temperature for TGS at 20 W evident towards the very end of the experiment may be indicative of a lower insulation temperature that causes the sample to cool more rapidly after the power is turned off. However, the TGS temperature directly after power-off was found to be significantly higher as compared to $CaCO_3$.

Evidence herein suggests that the HT range could be reached experimentally, although it should be considered whether a similar amount (or less) of TGS can be used and concentrated into a tumor site with similar results. Future results that indicate a slowdown at $T_C$ but marginally exceeding this value should not be surprising in this dense powder form, for the material, though in the paraelectric phase, may still have a tendency to heat due to dielectric losses.

As discussed above, TGS was mixed with PLGA to show the possibility for TGS to be encapsulated by a material less soluble in water. The results of temperature rise for these samples are given below. For the sample of TGS/PLGA, the sample temperature rise was found to be highly repeatable. TGS/PLGA samples tested showed a smaller temperature rise than TGS alone.

Figure 6:
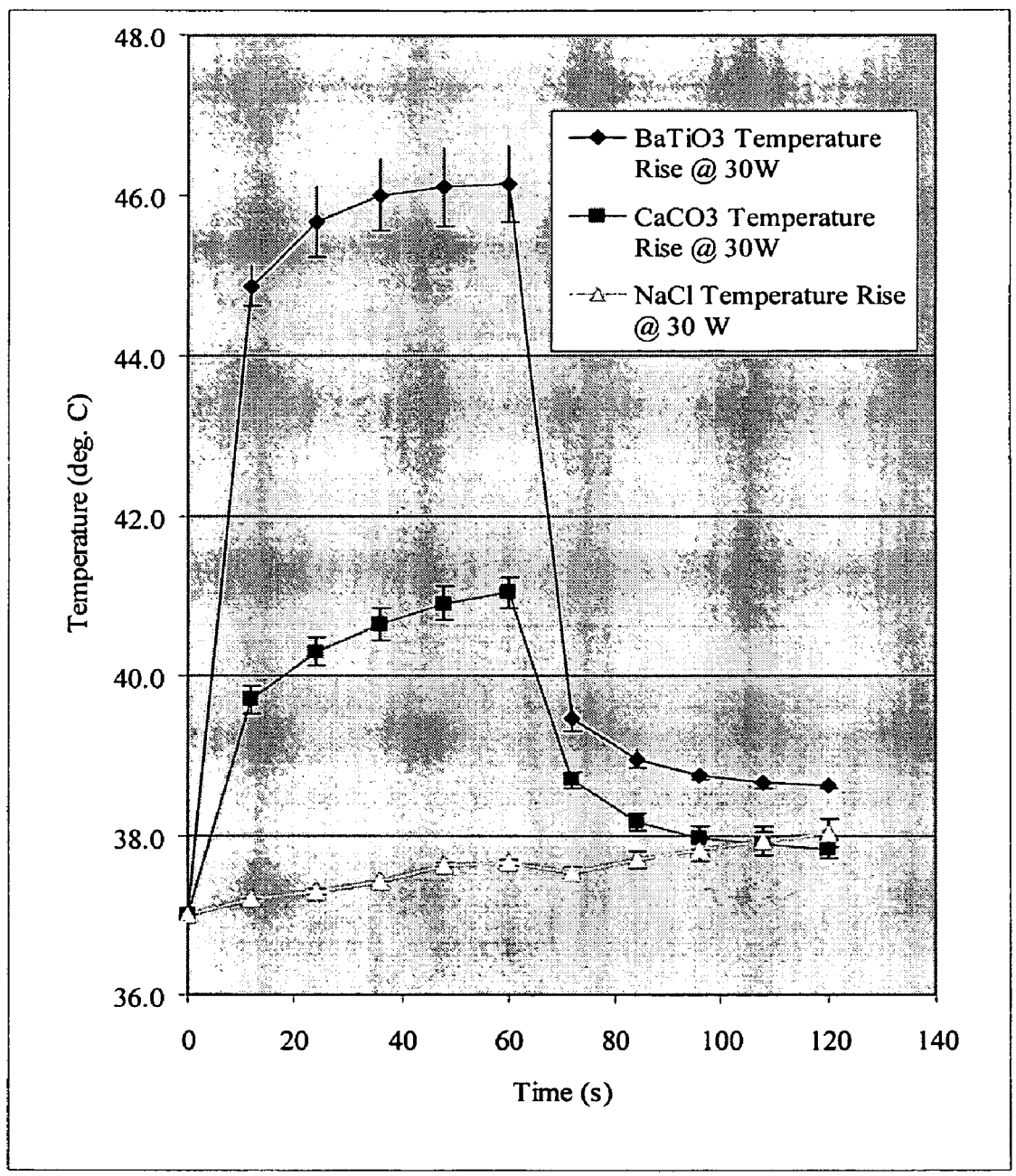
FIG. 6 shows data comparing the temperature profiles obtained for TGS/PLGA and $CaCO_3$ using an applied power of 20 W.

A comparison of the temperature profiles for TGS/PLGA and $CaCO_3$ at 20 W is given in FIG. 6. It can be seen that TGS/PLGA heats up significantly faster as compared to the control.

BT samplers were also tested. A rather large increase in temperature was found within the first 12 s of testing. This is quite consistent in testing both TGS and BT. The temperature does not instantaneously increase within the first 12 s. Rather, there is a smaller "jump" than that shown in the diagram and subsequent smaller increases until it reaches the standard asymptotic behavior. The acute jump may signal some RF interference, but RF interference would not explain the magnitude of the increase, especially over control (tests are shown in this section for $CaCO_3$ and NaCl at similar mass). The rather precipitous drop in temperature towards the end of the power-on cycle is troublesome. One would expect, as in TGS, the material to retain much more of the heat produced as suggested by the temperature rise graph. The difficulty is in merely attributing this behavior to RF interference in the thermocouple tip in light of results on $CaCO_3$.

Figure 7:
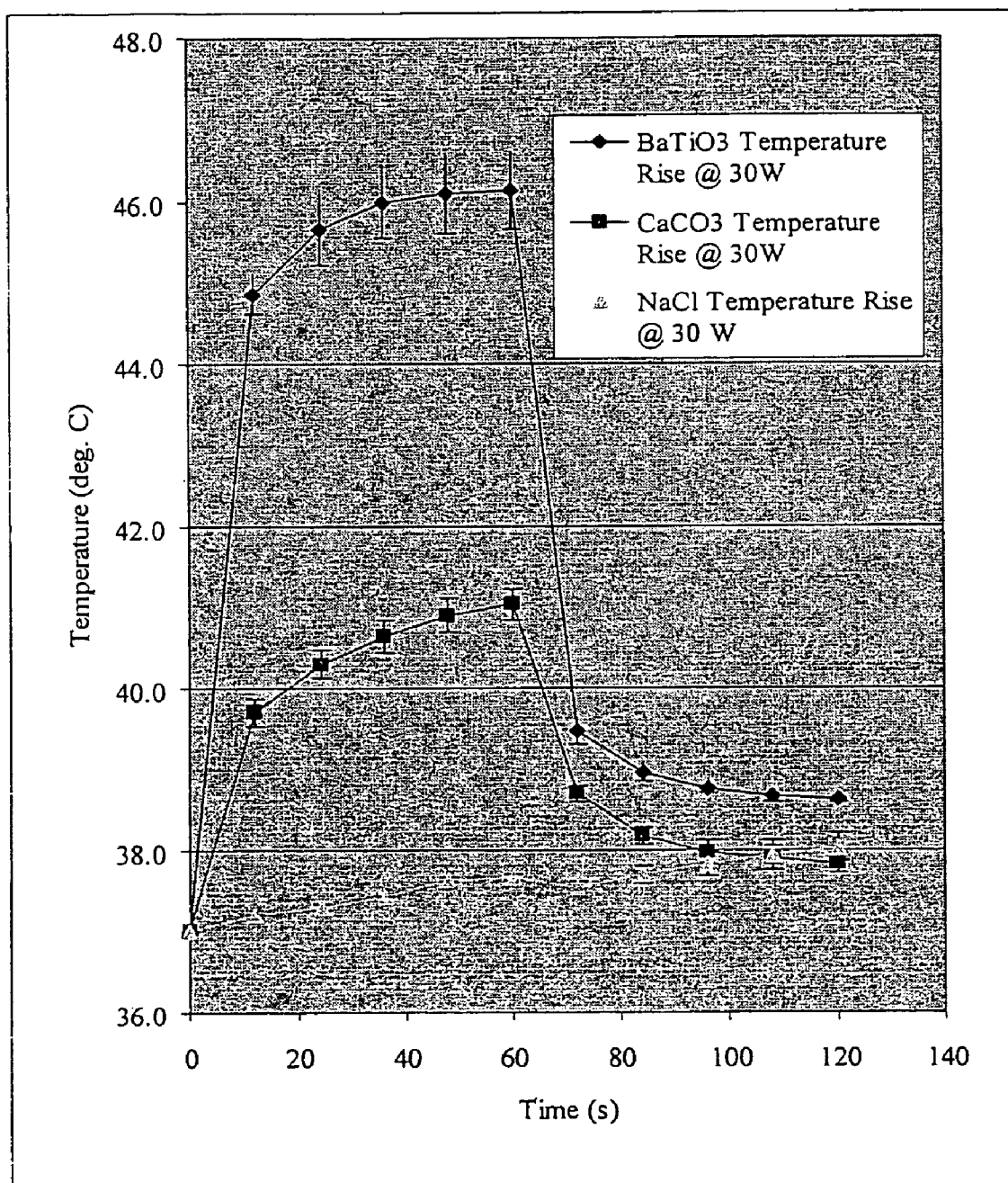
FIG. 7 shows the temperature dynamics of a BT sample responsive to FE heating.

FIG. 7 shows evidence of a more profound temperature increase in BT than other materials. The BT sample gives a higher remaining temperature at the 72 s mark, giving greater evidence for FE heating over RF interference alone. The shape of the temperature profile and the magnitude of increased temperature over control samples are comparable to that of TGS, though with a greater maximum temperature.

The heating curves obtained generally were found to follow the expected theoretical behavior. All FE temperature rise figures obtained show an asymptotic behavior in the matter of a minute, and prolonged testing of FEs show no marked difference from this asymptotic heating behavior.

The experimental data obtained demonstrates that FE materials respond better to EM fields as compared to normal dielectrics. Generally, the temperature rise was much more significant in the FEs than in the control dielectrics. BT performed better than TGS, which is to be anticipated due to its higher polarization. TGS also heated well compared to the dielectric controls, and it demonstrated strong temperature increases even when dispersed in a PLGA polymer matrix. This proves that TGS can heat at a given site even when present within a biodegradable coating material.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

The invention claimed is:

1. A method of localized cell heating, comprising the steps of:
   introducing a plurality of ferroelectric comprising particles into a target region of a patient, and
   applying a time varying electrical field to said target region, wherein said ferroelectric particles absorb energy from said electrical field and heat said target region in response.

2. The method of claim 1, wherein said electrical field is a pulsed electrical field.

3. The method of claim 1, wherein said ferroelectric particles exhibit a Curie Temperature (Tc) in a therapeutic range between 41.5° C. and 50° C.

4. The method of claim 1, wherein said ferroelectric particles comprise TGS.

5. The method of claim 1, wherein said ferroelectric particles comprise at least two different ferroelectric materials.

6. The method of claim 1, wherein said ferroelectric particles comprise doped TGS.

7. The method of claim 1, wherein said plurality of ferroelectric comprising particles comprise a non-ferroelectric coating layer on ferroelectric cores.

8. The method of claim 1, wherein said coating layer comprises a bio-compatible and biodegradable polymer, said polymer selected from the group consisting of PLGA, PLA and PGA.

9. The method of claim 8, wherein at least one drug is included beneath said coating layer.

10. The method of claim 1, wherein said plurality of particles have an average largest dimension of less than 15 µm and are disposed in a pharmaceutically suitable solution, wherein said introducing step comprises injection of said solution into said target region of said patient.

* * * * *

UNITED STATES PATENT AND TRADEMARK OFFICE
CERTIFICATE OF CORRECTION

PATENT NO. : 7,632,295 B2
APPLICATION NO. : 11/512528
DATED : December 15, 2009
INVENTOR(S) : Glen Patrick Flores and Christopher D. Batich It is certified that error appears in the above-identified patent and that said Letters Patent is hereby corrected as shown below:

Column 5,
Line 51, "dielectric-constant" should read --dielectric constant--

Signed and Sealed this

Twenty-third Day of March, 2010

David J. Kappos
*Director of the United States Patent and Trademark Office*